(12) United States Patent
Queen et al.

(10) Patent No.: US 12,420,064 B2
(45) Date of Patent: Sep. 23, 2025

(54) PERIPHERALLY INSERTED CENTRAL-LINE CATHETER (PICC) LINE SUPPORT APPARATUS

(71) Applicants: Eric Scott Queen, Waxhaw, NC (US); Deborah Fryer Queen, Waxhaw, NC (US); Lillian Grace Queen, Waxhaw, NC (US)

(72) Inventors: Eric Scott Queen, Waxhaw, NC (US); Deborah Fryer Queen, Waxhaw, NC (US); Lillian Grace Queen, Waxhaw, NC (US)

(73) Assignee: Covena, LLC, Waxhaw, NC (US)

( * ) Notice: Subject to any disclaimer, the term of this patent is extended or adjusted under 35 U.S.C. 154(b) by 798 days.

(21) Appl. No.: 17/618,756

(22) PCT Filed: Jun. 19, 2020

(86) PCT No.: PCT/US2020/038685
§ 371 (c)(1),
(2) Date: Dec. 13, 2021

(87) PCT Pub. No.: WO2020/257616
PCT Pub. Date: Dec. 24, 2020

(65) Prior Publication Data
US 2022/0257907 A1 Aug. 18, 2022

Related U.S. Application Data

(60) Provisional application No. 62/864,158, filed on Jun. 20, 2019.

(51) Int. Cl.
*A61M 25/02* (2006.01)
*A61M 25/00* (2006.01)

(52) U.S. Cl.
CPC ........ *A61M 25/02* (2013.01); *A61M 25/0017* (2013.01); *A61M 2025/0206* (2013.01); *A61M 2025/0213* (2013.01)

(58) Field of Classification Search
CPC .............. A61M 25/02; A61M 25/0017; A61M 2025/0206; A61M 2025/0213
See application file for complete search history.

(56) References Cited

U.S. PATENT DOCUMENTS

| 5,174,305 A | 12/1992 | Childs |
| D756,510 S | 5/2016 | Fitzgerald et al. |

(Continued)

FOREIGN PATENT DOCUMENTS

| CN | 205084769 U | 3/2016 |
| CN | 109173010 | 1/2019 |

OTHER PUBLICATIONS

International Search Report and Written Opinion; PCT/US2020/038685; Sep. 24, 2020; 5 pages.

(Continued)

*Primary Examiner* — Tasnim Mehjabin Ahmed
(74) *Attorney, Agent, or Firm* — Stanek Lemon Crouse & Meeks, PA

(57) ABSTRACT

A PICC line support apparatus can include a flexible conforming material forming a cylinder with a first opening and a second opening at opposite ends of the cylinder. A PICC line opening in the cylinder can be located between the opposite ends of the cylinder and a skirt can include the flexible conforming material, where the skirt can include a first end of the skirt that is coupled to the cylinder and including a second end of the skirt that is open and is separated from the first and second openings.

15 Claims, 10 Drawing Sheets

(56) References Cited

U.S. PATENT DOCUMENTS

| | | | |
|---|---|---|---|
| 2007/0083163 A1* | 4/2007 | Rydell | A61M 25/02 604/179 |
| 2008/0045906 A1* | 2/2008 | Grissom | A61M 25/02 604/179 |
| 2008/0208130 A1 | 8/2008 | Furman | |
| 2009/0234296 A1 | 9/2009 | Robison | |
| 2013/0012883 A1 | 1/2013 | Fitzgerald et al. | |
| 2018/0015258 A1 | 1/2018 | Shen | |
| 2019/0046772 A1 | 2/2019 | Jutras | |

OTHER PUBLICATIONS

International Preliminary Report on Patentability; PCT/US2020/038685; Dec. 30, 2021; 5 pages.
Extended European Search Report, Application No. EP 20 82 5995.2, dated Jun. 26, 2023, 7 pages.

\* cited by examiner

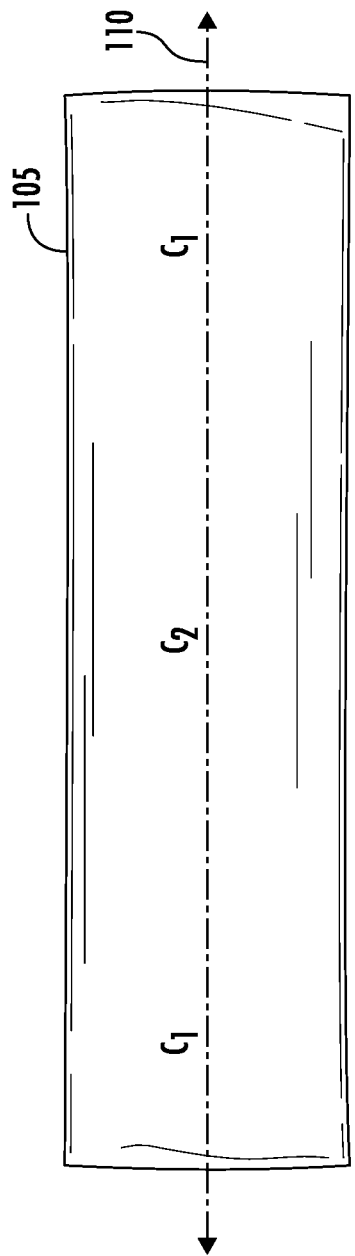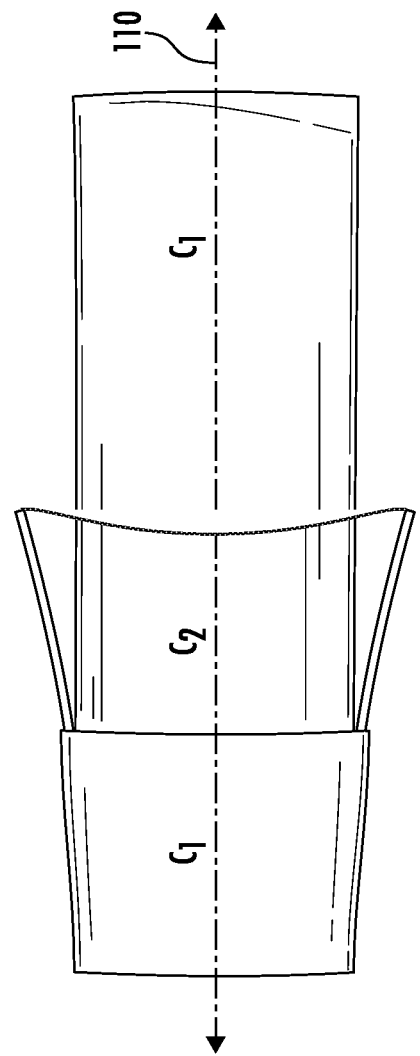

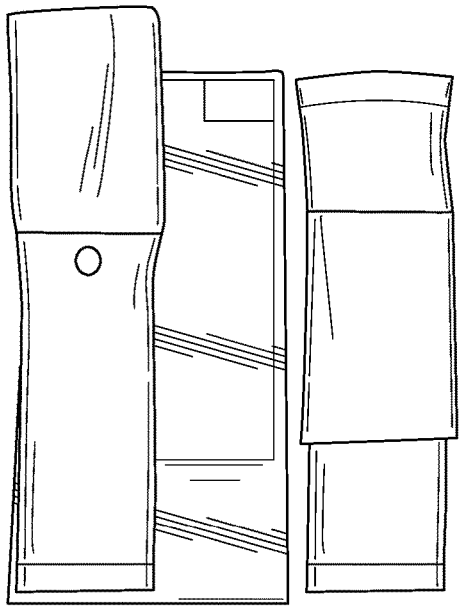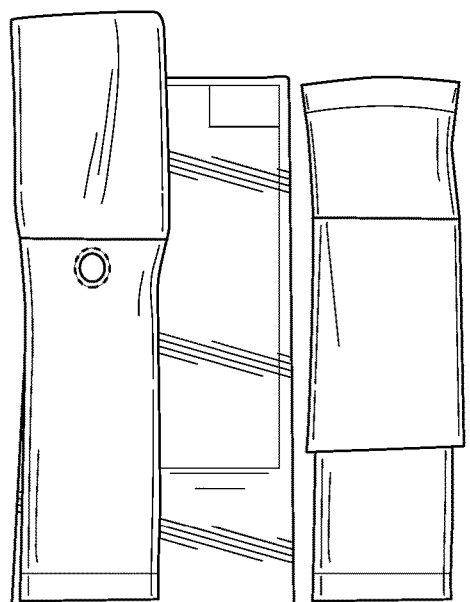
FIG. 7

PERIPHERALLY INSERTED CENTRAL-LINE CATHETER (PICC) LINE SUPPORT APPARATUS

CLAIM FOR PRIORITY

The present application is a 35 U.S.C. § 371 national phase application of PCT International Application No. PCT/US2020/038685, having an international filing date of Jun. 19, 2020, entitled Peripherally Inserted Central-Line Catheter (PICC) Line Support Apparatus which claims priority to U.S. Provisional Application No. 62/864,158, filed in the USPTO on Jun. 20, 2019, entitled Peripherally Inserted Central-Line Catheter (PICC) Line Support Apparatus Including PICC Line Cover Skirts and Related Devices, The disclosures of each application are incorporated by reference in their entireties. The above PCT International Application was published as International Publication No. WO 2020257616.

FIELD

This invention relates generally to catheters with injection ports, such as peripherally inserted central catheters, and more particularly to devices supporting the use of peripherally inserted central catheters.

BACKGROUND

A peripherally inserted central catheter (PICC or PIC line), less commonly called a percutaneous indwelling central catheter, is a form of intravenous access that can be used for a prolonged period of time (e.g., for long chemotherapy regimens, extended antibiotic therapy, or total parenteral nutrition) or for administration of substances that should not be done peripherally (e.g., antihypotensive agents a.k.a. pressors). It is a catheter that enters the body through the skin (percutaneously) at a peripheral site, extends to the superior vena cava (a central venous trunk), and stays in place (dwells within the veins) for days or weeks.

PICCs can remain in situ for extended periods of time (i.e., chronically), from seven days to up to 12 months. They are used in both the hospital and community settings. PICCs can be used for intravenous delivery of total parenteral nutrition (TPN), chemotherapy, antibiotics or other medications, and can also be used for blood sampling if the lumen is 4 French or larger in size.

SUMMARY

Embodiments according to the invention can provide peripherally inserted central-line catheter (PICC) line support apparatuses including picc line cover skirts and related devices. Pursuant to these embodiments, a PICC line support apparatus can include a flexible conforming material forming a cylinder with a first opening and a second opening at opposite ends of the cylinder. A PICC line opening in the cylinder can be located between the opposite ends of the cylinder and a skirt can include the flexible conforming material, where the skirt can include a first end of the skirt that is coupled to the cylinder and including a second end of the skirt that is open and is separated from the first and second openings.

In some embodiments according to the invention, PICC line support apparatus can include a flexible conforming material forming a cylinder with a first opening and a second opening at opposite ends of the cylinder. A PICC line opening in the cylinder can be located between the opposite ends of the cylinder and a skirt can include a first end of the skirt that is coupled to the cylinder proximate to first opening and can include a second end of the skirt that is open and encircles the cylinder facing the second opening.

In some embodiments according to the invention, a PICC line support apparatus can include a flexible conforming material forming a cylinder with a first opening and a second opening at opposite ends of an axis of the cylinder. A PICC line opening can be in the cylinder located between the opposite ends of the cylinder and a skirt can be moveable along the axis on the cylinder to obscure or expose the PICC line opening without moving the first or second opening in the cylinder.

BRIEF DESCRIPTION OF THE DRAWINGS

FIGS. 6A and 6B are cross-sectional views illustrating partial formation of a PICC line support apparatus in a relaxed (or unused) state including a sleeve in the shape of a cylinder and a skirt that is moveable on the cylinder to obscure or expose a PICC line opening in the cylinder by folding a portion of the cylinder in FIG. 6A back on itself to form a double thickness portion of the cylinder that encircles the adjacent portion of the cylinder and that can be coupled to the cylinder at one end whereas the opposite end of the skirt is left open in some embodiments according to the invention.

FIG. 7 is a collection of images of a PICC line support apparatus in a relaxed (or unused) state including a sleeve in the shape of a cylinder and a skirt that is moveable on the cylinder to obscure or expose a PICC line opening in the cylinder in some embodiments according to the invention.

DETAILED DESCRIPTION OF EMBODIMENTS ACCORDING TO THE INVENTION

Exemplary embodiments of the present disclosure are described in detail with reference to the accompanying drawings. The disclosure may, however, be exemplified in many different forms and should not be construed as being limited to the specific exemplary embodiments set forth herein. Rather, these exemplary embodiments are provided so that this disclosure will be thorough and complete, and will fully convey the scope of the disclosure to those skilled in the art.

Figure 1:
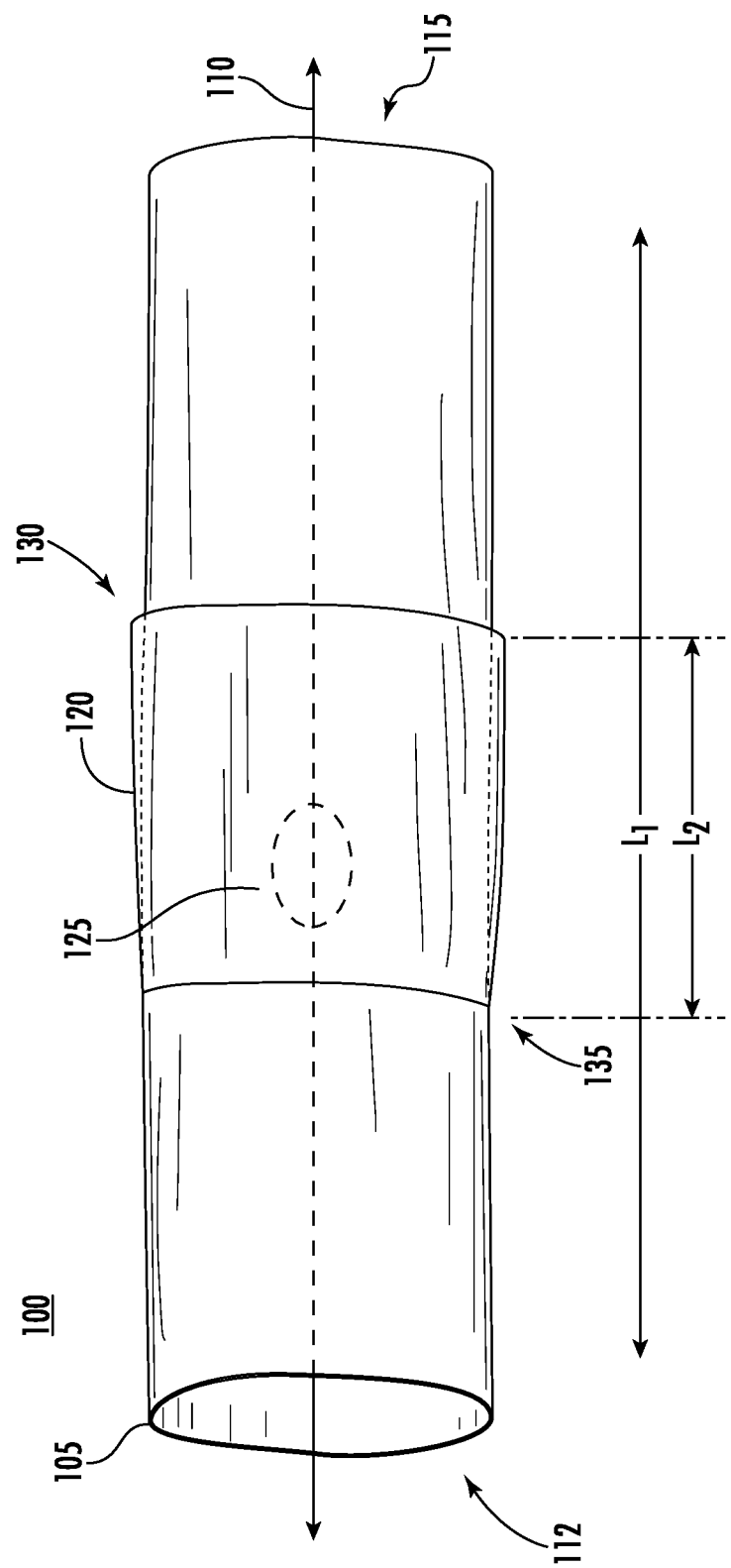
FIG. 1 is a schematic diagram of a PICC line support apparatus in a relaxed (or unused) state including a sleeve in the shape of a cylinder and a skirt that is moveable on the cylinder to obscure or expose a PICC line opening in the cylinder in some embodiments according to the invention.

FIG. 1 is a schematic diagram of a PICC line support apparatus 100 in a relaxed (or unused) state including a sleeve in the shape of a cylinder 105 and a skirt that is moveable on the cylinder to obscure or expose a PICC line opening (whether in use via an infusion or not) in the cylinder in some embodiments according to the invention. According to FIG. 1, the cylinder 105 includes a first opening 112 and a second opening 115 located at the opposite ends of the cylinder 105. The cylinder 105 is defined by an axis 110 that extends along the longitudinal direction of the cylinder 105 and intersects both the first opening 112 and the second opening 115. The interior of the cylinder 105 defines a sleeve through which a patient's arm (or other body part as illustrated, for example in FIG. 8) can be inserted. The cylinder 105 has an overall length L1 that extends from the first opening 112 to the second opening 115 in the relaxed state.

As further shown in FIG. 1, the cylinder 105 includes a skirt 120 that overlaps a portion of the cylinder 105 and is coupled to the cylinder 105 at a first end of the skirt 135 but remains open at a second end of the skirt 130 that opposite from the first end of the skirt 135. It will be understood that the first end of the skirt 135 can be fastened to the cylinder 105 at the position to the left of the PICC line opening 125. As shown in FIG. 1, the second end of the skirt 130 is open and is not coupled to the cylinder 105. It will be understood that the use of the term "second end of the skirt" refers to the portion of the skirt 120 that forms the opening and does not necessarily mean the material used to form the skirt ends at the opening. For example, in some embodiments as shown in FIGS. 6A and 6B, the skirt can be formed by doubling back the material used to form the cylinder.

Moreover, the second end of the skirt 130 encircles the cylinder 105 and remains free so as to be moveable along the cylinder in the longitudinal direction 110. As shown the second end of the skirt 130 extends along the cylinder 105 to the right side of the PICC line opening 125 so that skirt 120 bridges the PICC line opening 125 in the relaxed state.

Still referring to FIG. 1, the cylinder 105 includes a PICC line opening 125 that is configured to allow insertion there through by a PICC line that may be chronically inserted into a patient for the administration of therapies under the supervision of a medical doctor. As further shown in FIG. 1, the skirt 120 is configured to move relative to the first end of the skirt 135 to expose the PICC line opening 125 in a first position to obscure the pic line open 125 in a second position. In some embodiments according to the invention, the skirt 125 has a second length L2 that is less than the length L1 of the cylinder 105 in the relaxed state.

In some embodiments according to the invention, the cylinder 105 is made from a flexible conforming material such as a woven or knitted fabric that includes and an elastic material such that the cylinder 105 can be stretched over and conform to an appendage comfortably. In some embodiments according to the invention, the flexible conforming material can be Lycra or other nylon based material. In some embodiments according to the invention, the flexible conforming material can be neoprene.

Figure 2:
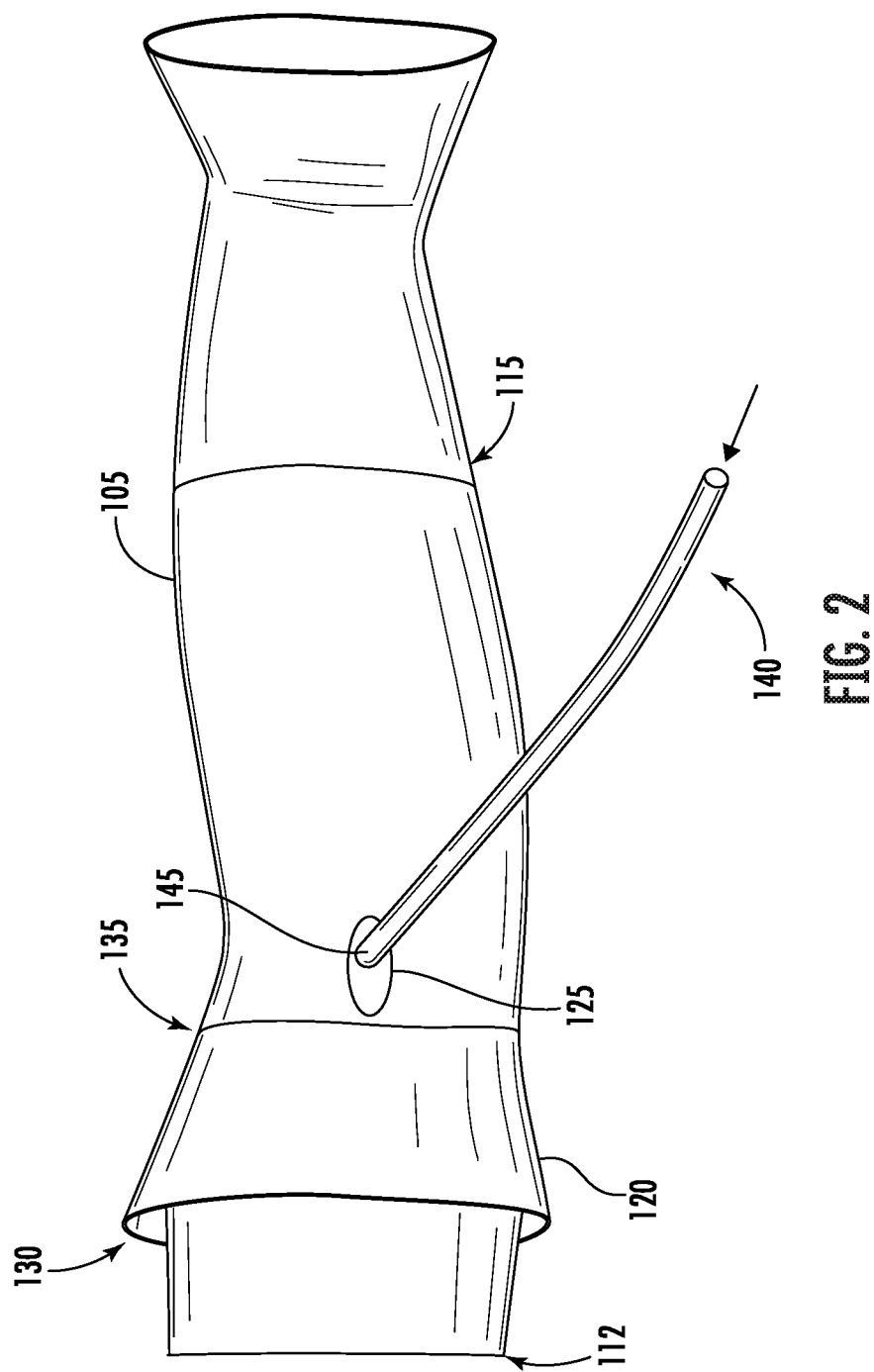
FIG. 2 is a schematic diagram of a PICC line support apparatus in a compressed (or used) state including a sleeve in the shape of a cylinder and a skirt exposing a PICC line opening in the cylinder and a PICC line extending through the opening in some embodiments according to the invention.

FIG. 2 is a schematic diagram of a PICC line support apparatus in a compressed (or used) state where the cylinder acts as a sleeve on the arm of a patient where the skirt exposes the PICC line opening 125 having a PICC line extending therethrough in some embodiments according to the invention. According to FIG. 2, when the cylinder 105 (sleeve) is in the used state (such as on the arm of a patient) the skirt 120 can be folded back toward the first opening 112 to expose the PICC line opening 125 so that an infusion can be provided to the patient via a catheter 140. It will be understood that although FIG. 2 shows the PICC line opening 125 as exposed during the infusion, the skirt 120 maybe moved to cover the PICC line opening 125 during the infusion. In some embodiments, the skirt 120 and the skirt opening 125 are configured to conceal and stabilize a container of medication (such as those used for chemotherapy) during the infusion. In some embodiments, the skirt 120 and the skirt opening 125 are configured to conceal and stabilize a heat or ice pack.

Figure 3:
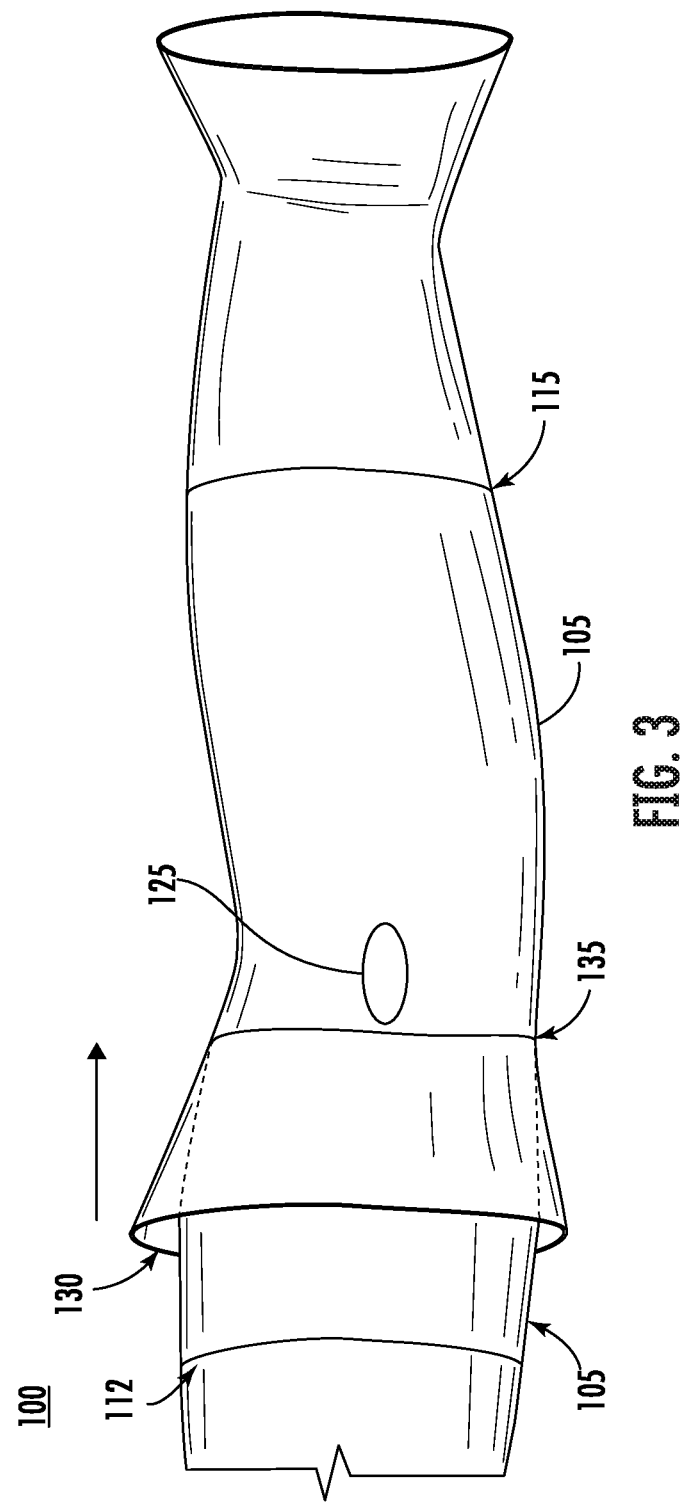
FIG. 3 is a schematic diagram of a PICC line support apparatus in a compressed (or used) state including a sleeve in the shape of a cylinder and a skirt exposing a PICC line opening in the cylinder where the skirt is being moved to partially obscure the PICC line opening in some embodiments according to the invention.

FIG. 3 is a schematic diagram of a PICC line support apparatus 100 in a compressed (or used) where the cylinder acts as a sleeve on the arm of a patient and the skirt 120 exposes the PICC line opening 125 in some embodiments according to the invention. Accordingly, it will be understood that FIG. 3 can illustrate implementation on the patient after an infusion such as that shown in FIG. 2, where the skirt 120 is being moved to partially obscure the PICC line opening 125 in some embodiments according to the invention. In particular, after the infusion the skirt 120 can be folded away from the first opening 112 toward the second opening 115 to (partially) obscure the PICC line opening 125. As described above in reference to FIG. 2, in some embodiments, the skirt 120 can be folded to (partially) obscure the PICC line opening 125 during the infusion.

Figure 4:
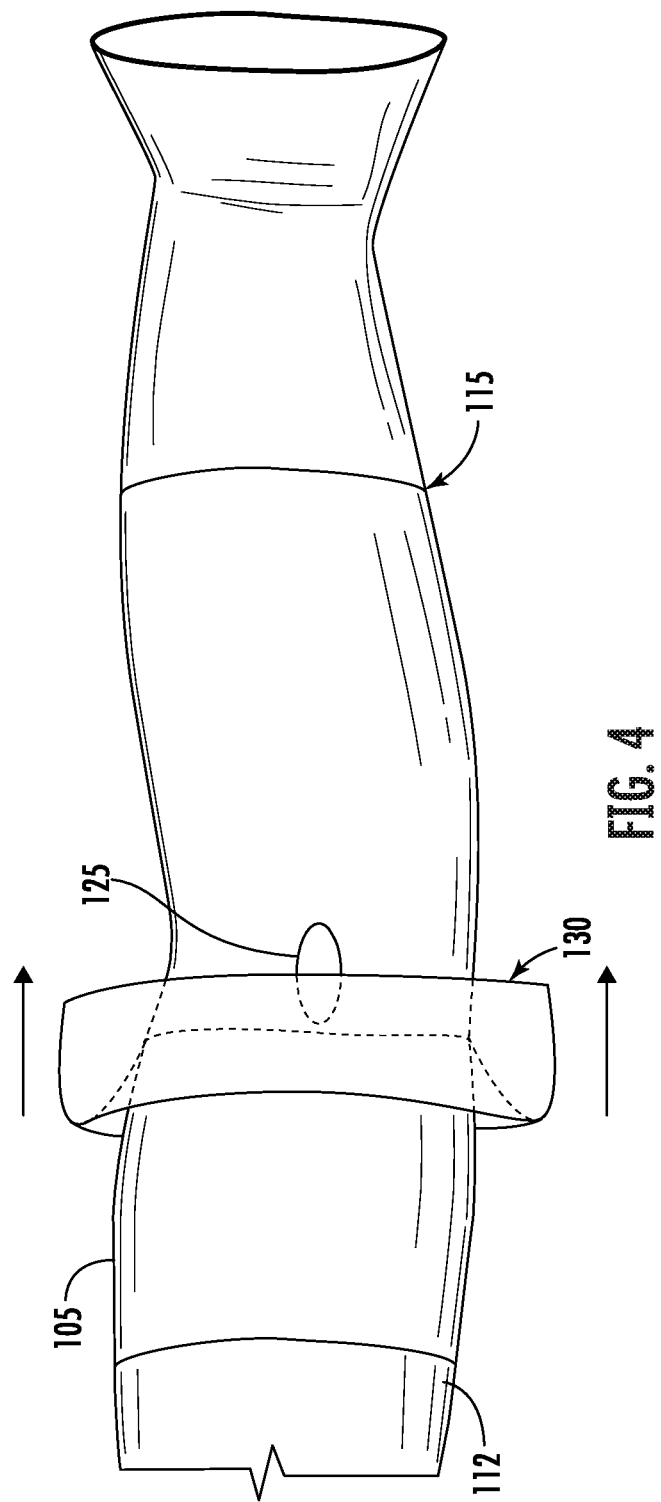
FIG. 4 is a schematic diagram of a PICC line support apparatus in a compressed (or used) state including a sleeve in the shape of a cylinder and a skirt exposing a PICC line opening in the cylinder where the skirt is being further moved (relative to FIG. 3) to increasingly obscure the PICC line opening in some embodiments according to the invention.

FIG. 4 is a schematic diagram of a PICC line support apparatus 100 in a compressed (or used) where the cylinder acts as a sleeve on the arm of a patient and the skirt 120 partially exposes the PICC line opening 125 in some embodiments according to the invention. Accordingly, it will be understood that FIG. 4 can illustrate implementation on the patient after an infusion such as that shown in FIG. 2, where the skirt 120 is being moved to further partially obscure the PICC line opening 125 in some embodiments according to the invention. In particular, relative to the position shown in FIG. 3, the skirt 120 can be further folded away from the first opening 112 toward the second opening 115 to more fully obscure the PICC line opening 125. As described above in reference to FIG. 3, in some embodiments, the skirt 120 can be folded to (partially) obscure the PICC line opening 125 during the infusion.

Figure 5:
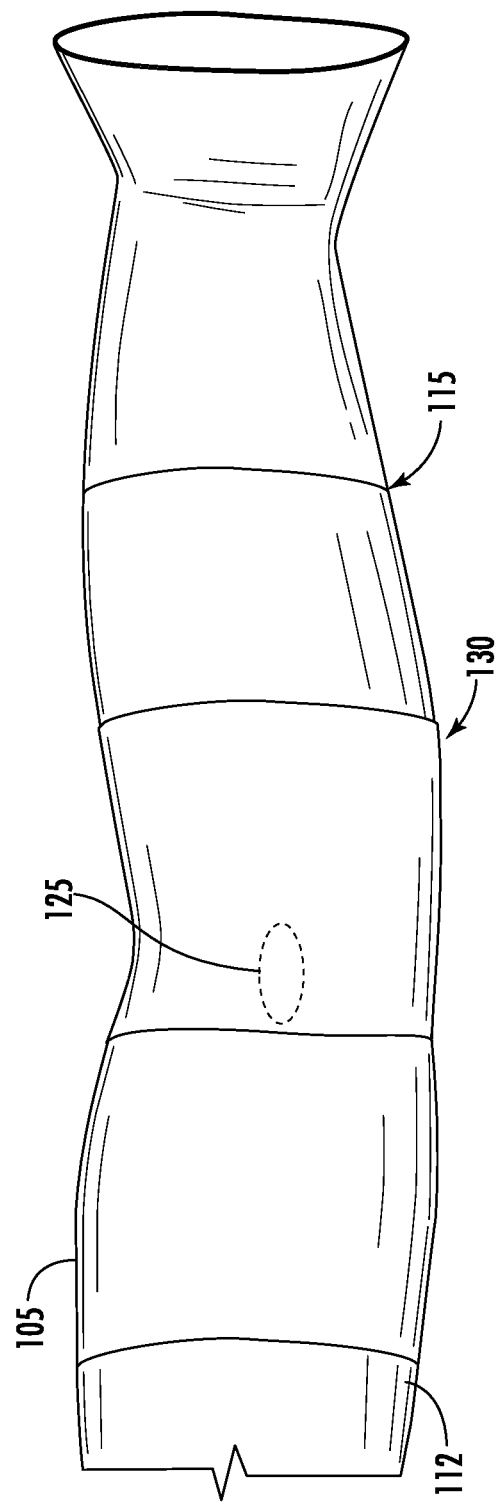
FIG. 5 is a schematic diagram of a PICC line support apparatus in a compressed (or used) state including a sleeve in the shape of a cylinder and a skirt exposing a PICC line opening in the cylinder where the skirt further moved (relative to FIGS. 3 and 4) to completely obscure the PICC line opening in some embodiments according to the invention.

FIG. 5 is a schematic diagram of a PICC line support apparatus 100 in a compressed (or used) where the cylinder acts as a sleeve on the arm of a patient and the skirt 120 fully obscures the PICC line opening 125 in some embodiments according to the invention. Accordingly, it will be understood that FIG. 5 can illustrate implementation on the patient after an infusion such as that shown in FIG. 2, where the skirt 120 has been moved to fully obscure the PICC line opening 125 in some embodiments according to the invention. In particular, relative to the position shown in FIG. 4, the skirt 120 is further folded away from the first opening 112 toward the second opening 115 to fully obscure the PICC line opening 125. As described above in reference to FIG. 3, in some embodiments, the skirt 120 can be folded to fully obscure the PICC line opening 125 during the infusion.

FIGS. 6A and 6B are cross-sectional views illustrating partial formation of a PICC line support apparatus in a relaxed (or unused) state including a sleeve in the shape of a cylinder and a skirt that is moveable on the cylinder to obscure or expose a PICC line opening in the cylinder by folding a portion of the cylinder in FIG. 6A back on itself to form a double thickness portion of the cylinder that encircles the adjacent portion of the cylinder and that can be coupled to the cylinder at one end whereas the opposite end of the skirt is left open in some embodiments according to the invention. In some embodiments, the sections of the cylinder can be formed to apply different amounts of compression when worn. For example, the outermost portions (outside the portion concealed by the skirt when worn) can provide a first compression whereas the section between the outermost portions (i.e., the portion concealed by the skirt when worn) applies a second compression which can be less than the first compression to compensate for the doubling of the material that forms the cylinder under the skirt when used to conceal the PICC line opening.

It will be further understood that the apparatus shown herein may also be used on other parts of the body. For example, embodiments may be provided for use on the neck of a patient, the torso, the leg, or other body part, as illustrated in FIGS. 8-10.

Figure 8:
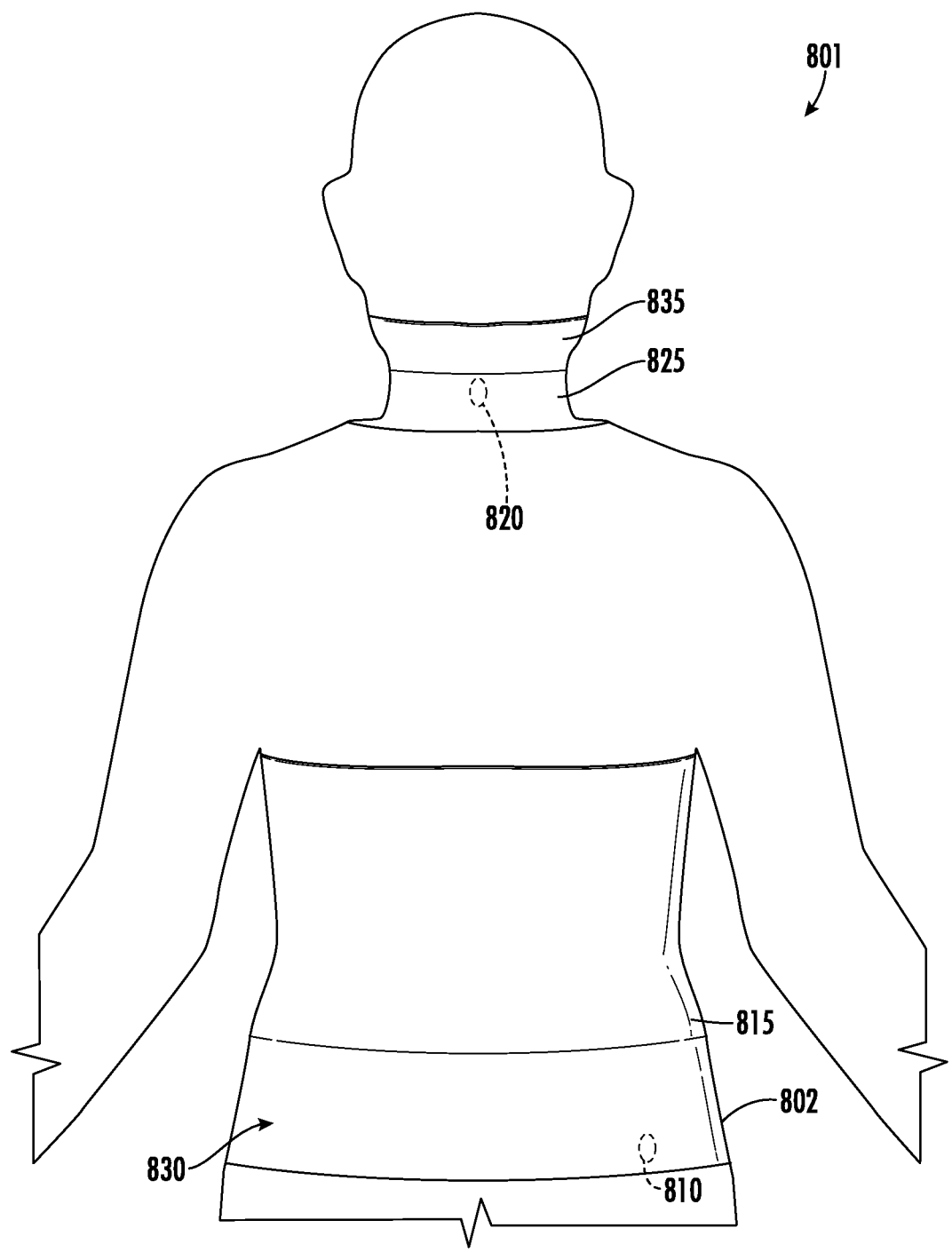
FIG. 8 is a schematic diagram of a patient neck and torso having a tracheostomy tube support apparatus and a gastrostomy tube support apparatus fitted, respectively, in some embodiments according to the invention.

FIG. 8 is a schematic diagram of a patient neck and torso having a tracheostomy tube support apparatus 801 and a gastrostomy tube support apparatus 802 fitted, respectively, in some embodiments according to the invention. It will be understood that the tracheostomy tube support apparatus 801 and the gastrostomy tube support apparatus 802 can be analogous in structure and function to the other embodiments disclosed herein (such as those shown in FIGS. 3-5). As shown in FIG. 8, skirts 825 and 830 are moveable to cover/expose a tracheostomy tube opening 820 and a gastrostomy tube opening 810.

Figure 9:
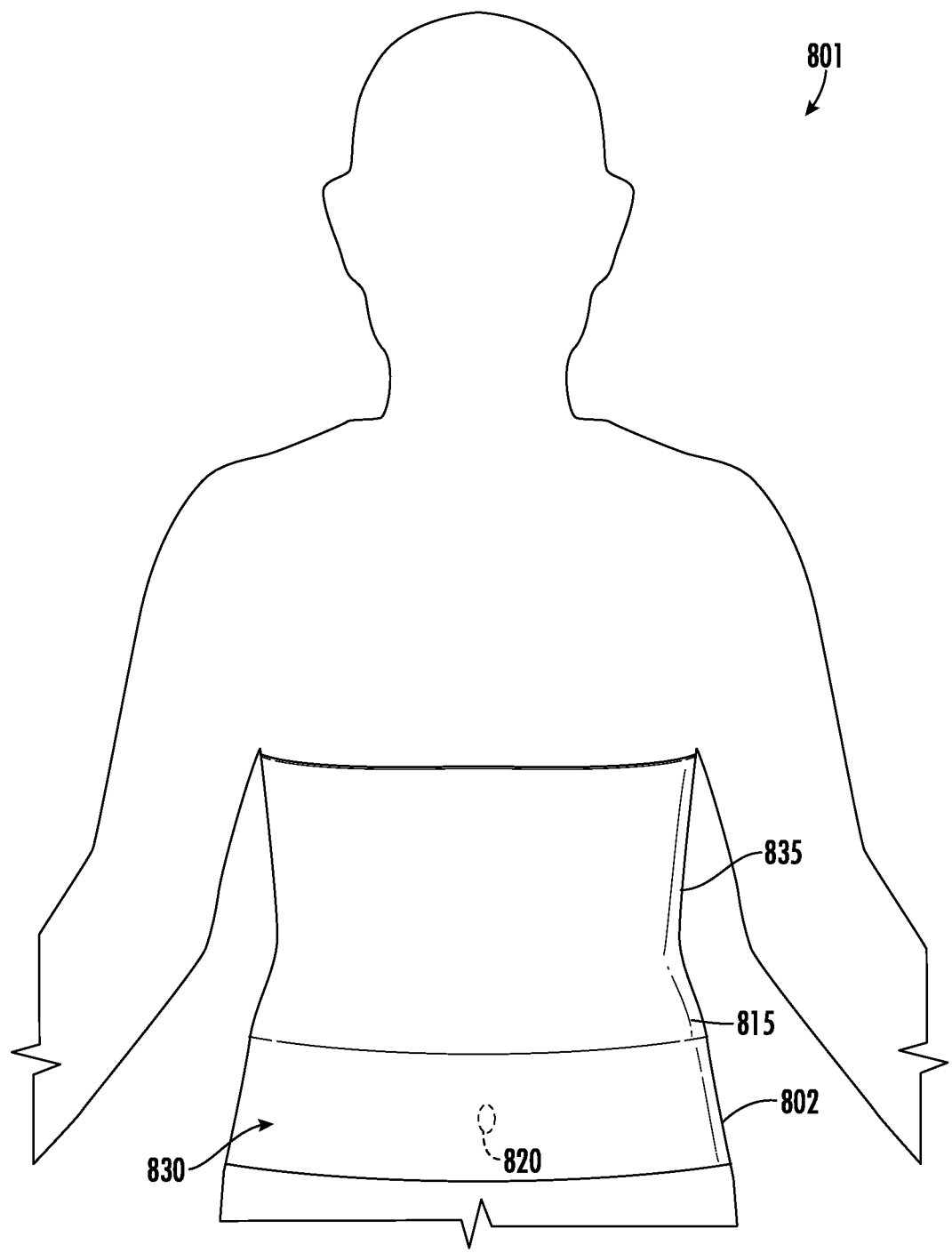
FIG. 9 is a schematic diagram of a tracheostomy tube support apparatus of FIG. 8 in a compressed (or used) state including a sleeve in the shape of a cylinder and a skirt exposing a tracheostomy tube opening in the cylinder where the skirt is being moved to partially obscure the tracheostomy tube opening in some embodiments according to the invention.

FIG. 9 is a schematic diagram of the tracheostomy tube support apparatus 801 of FIG. 8 in a compressed (or used) state including a sleeve 835 in the shape of a cylinder and the skirt 825 exposing the tracheostomy tube opening 820 in the cylinder where the skirt 825 is being moved to cover the tracheostomy tube opening 820 in some embodiments according to the invention.

Figure 10:
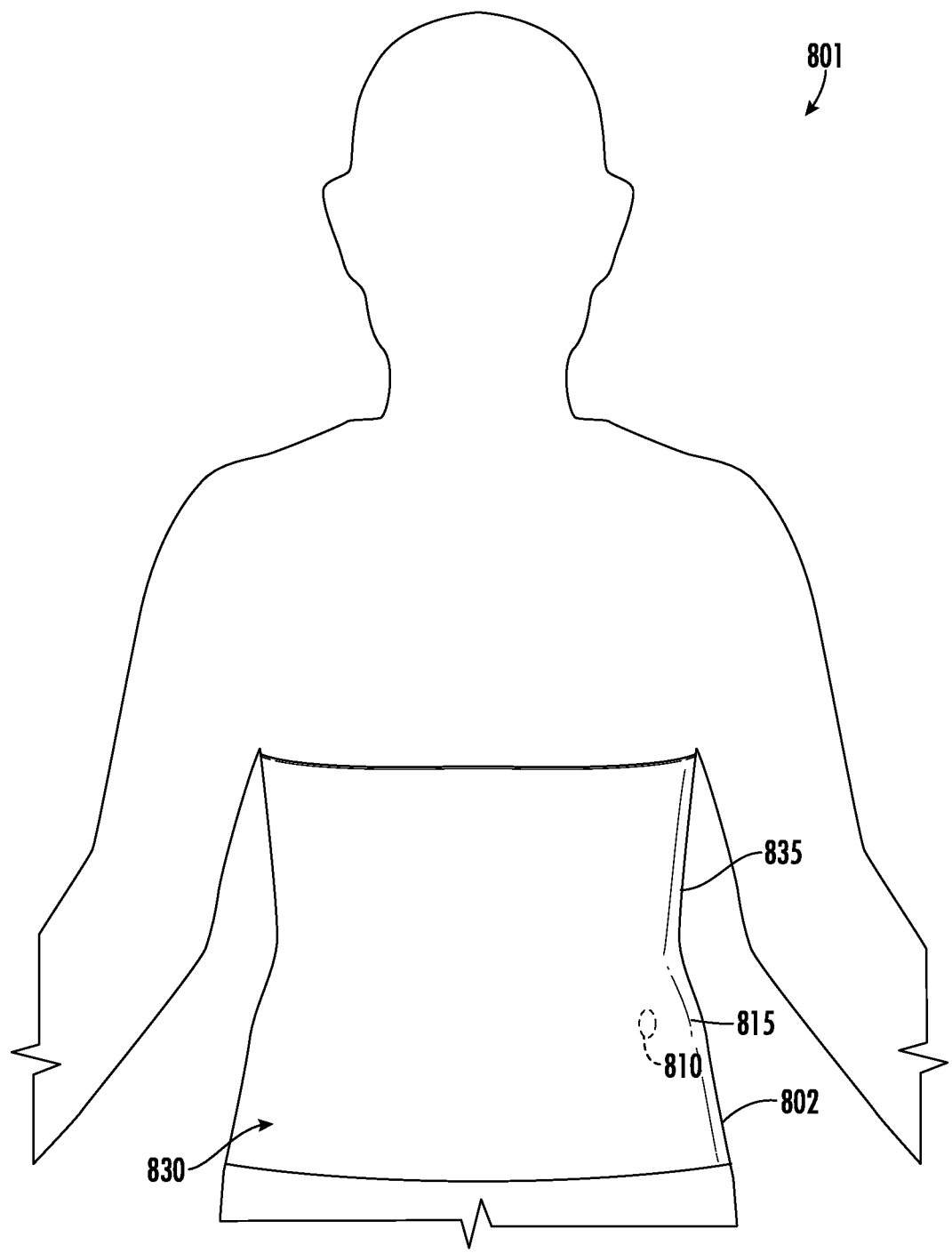
FIG. 10 is a schematic diagram of a gastrostomy tube support apparatus of FIG. 8 in a compressed (or used) state including a sleeve in the shape of a cylinder and a skirt exposing a gastrostomy tube opening in the cylinder where the skirt is being moved to partially obscure the gastrostomy tube opening in some embodiments according to the invention.

FIG. 10 is a schematic diagram of a gastrostomy tube support apparatus 802 of FIG. 8 in a compressed (or used) state including the sleeve 815 in the shape of a cylinder and the skirt 830 exposing the gastrostomy tube opening 810 in the cylinder where the skirt 830 is being moved to cover the gastrostomy tube opening 810 in some embodiments according to the invention.

What is claimed:

1. A peripherally inserted central-line catheter (PICC) line support apparatus comprising:
   a flexible conforming material forming a cylinder with a first opening and a second opening at opposite ends of the cylinder;
   a PICC line opening in the cylinder located between the opposite ends of the cylinder; and
   a separate skirt comprising the flexible conforming material, the skirt including a first end of the skirt that is coupled to the cylinder and including a second end of the skirt that is open and is separated from the first opening and the second opening, the separate skirt moving from a first position relative to the cylinder and a second position relative to the cylinder.

2. The PICC line support apparatus of claim 1 wherein the second end of the skirt is decoupled from the cylinder.

3. The PICC line support apparatus of claim 2, wherein the cylinder has a length from the first opening to the second opening in a relaxed state and the skirt has a length in the relaxed state that is less than the length of the cylinder in the relaxed state.

4. The PICC line support apparatus of claim 3 wherein the first end and the second end of the skirt are located on opposite sides of the PICC line opening relative to the first opening and the second opening when the cylinder is in the relaxed state.

5. The PICC line support apparatus of claim 3 wherein the relaxed state is provided when the PICC line support apparatus is unused.

6. The PICC line support apparatus of claim 5 wherein the cylinder has a length in a compression state that is provided when the PICC line support apparatus is worn on a body part.

7. The PICC line support apparatus of claim 1 wherein the flexible conforming material provides different amounts of compression adjacent to the PICC line opening and adjacent to the first opening of the cylinder and the second opening of the cylinder when the cylinder is in a compression state.

8. The PICC line support apparatus of claim 1 wherein the cylinder is seamless in a longitudinal dimension extending from the first opening to the second opening.

9. The PICC line support apparatus of claim 1 wherein the flexible conforming material comprises a knitted elastic material.

10. The PICC line support apparatus of claim 1 wherein the cylinder provides a sleeve configured to receive a patient's arm extending through the first and second openings.

11. The PICC line support apparatus of claim 10 wherein the PICC line opening is configured to expose a PICC line installed in the patient's arm.

12. The PICC line support apparatus of claim 10 wherein the skirt is configured to obscure the PICC line installed in the patient's arm when the skirt is placed at the first position on the cylinder and to expose the PICC line installed in the patient's arm when the skirt is placed at the second position on the cylinder.

13. The PICC line support apparatus of claim 12 wherein the skirt is configured to obscure the PICC line installed in the patient's arm during an infusion to the patient via the PICC line installed in the patient's arm.

14. A peripherally inserted central-line catheter (PICC) line support apparatus comprising:

a flexible conforming material forming a cylinder with a first opening and a second opening at opposite ends of the cylinder;

a PICC line opening in the cylinder located between the opposite ends of the cylinder; and a separate skirt including a first end of the skirt that is coupled to the cylinder proximate to first opening and including a second end of the skirt that is open and encircles the cylinder facing the second opening, the skirt moving between a first position relative to the cylinder and the PICC line and a second position relative to the cylinder and the PICC line.

15. A peripherally inserted central-line catheter (PICC) line support apparatus comprising:

a flexible conforming material forming a cylinder with a first opening and a second opening at opposite ends of an axis of the cylinder;

a PICC line opening in the cylinder located between the opposite ends of the cylinder; and a separate skirt moveable along the axis on the cylinder to obscure or expose the PICC line opening without moving the first or second opening in the cylinder.

* * * * *